United States Patent [19]
Maeda et al.

[11] Patent Number: 6,043,268
[45] Date of Patent: *Mar. 28, 2000

[54] AGENT FOR TREATMENT OF VIRAL INFECTIONS

[75] Inventors: Hiroshi Maeda, 21-19, Hotakubo 3-chome, Kumamoto-shi, Kumamoto 862, Japan; Takaaki Akaike, Kumamoto, Japan

[73] Assignee: Hiroshi Maeda, Kumamoto-ken, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/772,852

[22] Filed: Dec. 24, 1996

Related U.S. Application Data

[63] Continuation-in-part of application No. PCT/JP95/00065, Jan. 23, 1995.

[30] Foreign Application Priority Data

Jun. 29, 1994 [JP] Japan ..................................... 6-171946

[51] Int. Cl.⁷ .......................... A01N 43/50; A01N 37/52; A61K 38/00
[52] U.S. Cl. ............................. 514/401; 514/634; 514/21; 514/12
[58] Field of Search .................................... 514/401, 634, 514/21, 12

[56] References Cited

U.S. PATENT DOCUMENTS 5,633,230  5/1997  Twist et al. ............................... 514/15

FOREIGN PATENT DOCUMENTS

WO 14464  7/1994  WIPO .
WO 14465  6/1995  WIPO .

OTHER PUBLICATIONS

Nagai et al. 1993, 118CA:32560d.
Dawson et al. 1995, 123CA:160852r.
Twist et al. 1994, 121CA:149051s.
Docherly et al. 1987, 107CA:228522k.
Koprowski et al., Proc. Natl. Acad. Sci. USA, 90, 3024–3027 (1993).
Liu et al., Cancer Research, 52, 4139–4143 (1992).
Mollace et al., Biochemical and Biophysical Research Communications, 203, 87–92 (1994).
Karupiah et al., Science, 261, 1445–1448 (1993).
Croen, J. Clin. Invest., 91, 2446–2452 (1993).
Akaike et al., Biochemistry, 32, 827–832 (1993).
Jikken Kagaku, 11, No. 18, 38–42 (1993).
Akaike et al., J. NeuroVirology, 1, 118–125 (1995).
Dawson et al., Proc. Natl. Acad. Sci. USA, 90, 3256–3259 (1993).
Zheng et al., J. Virology, 67, No. 10, 5786–5791 (1993).
Mollace et al., Biochemical and Biophysical Research Communications, 194, No. 1, 439–445 (1993).
Pietraforte et al., J. Leukocyte Biology, 55, 175–182 (1994).
Melkova et al., Virology, 198, 731–735 (1994).
Butz et al., Microvial Pathogenesis, 16, 283–295 (1994).
J. Docherty, et al., Antimicrobial Agents and Chemotherapy, Oct. 1987, pp. 1562–1566.
Acker et al., Biochemical and Biophysical Research Communications, 214 (3) :755–759 (1995).
Nagai et al., Antiviral Research, 19:207–217 (1992).
Mitra 122 CA274115N, 1993.
Judd et al. 112 CA 51801a, 1990.

*Primary Examiner*—Russell Travers
*Attorney, Agent, or Firm*—Birch, Stewart, Kolasch & Birch, LLP

[57] ABSTRACT

A method for treatment of viral infections which comprises administering to the patients being suffering from said viral infections an effective amount of one or more substances selected from the group consisting of nitric oxide scavengers and nitric oxide synthase inhibitors. Said method for treatment of viral infections is useful in viral infections induced by influenza virus, herpes virus, hepatitis virus, cytomegalovirus, human immunodeficiency virus, etc.

8 Claims, 6 Drawing Sheets

6,043,268

AGENT FOR TREATMENT OF VIRAL INFECTIONS

This application is a continuation-in-part of PCT international application No. PCT/JP95/00065 which has an international filing date of Jan. 23, 1995 which designated the United States, the entire contents of which are hereby incorporated by reference.

TECHNICAL FIELD

The present invention relates to a method for treatment of viral infections. More particularly, the present invention relates to a method for treatment of infections induced by viruses such as influenza virus, herpes virus, hepatitis virus, cytomegalovirus, human immunodeficiency virus (HIV), etc.

BACKGROUND ART

Recently, it has been proved that nitric oxide radical (hereinafter, occasionally abbreviated as •NO) is an active principle of endothelium-derived relaxing factor, and acts as an mediator for the signal transduction mechanism of neural cells. On the other hand, since •NO is an unstable radical, the overproduction and release thereof have been considered to damage various cells and tissues with the chemical hyper-reactivity thereof. Besides, it has been recently reported that •NO is an important factor in the pathogenesis of endotoxin-induced shock such as septic shock.

Koprowski, et al. reported that inducible nitric oxide synthase (iNOS) is induced in the brain tissue by Borna disease virus, rabies virus, herpes simplex virus, and NO is produced by cells induced by iNOS, which may be a toxic factor accounting for neural cell damages [Hilary Koprowski, et al., Proc. Natl., Acad. Sci. USA, 90, pp 3024–3027 (1993)]. It has been also reported that NMMA ($N^G$-monomethyl-arginine), which is a nitric oxide synthase inhibitor, inhibits NO production which is induced by infection with Woodchuck hepatitis virus, and that formation of carcinogenic nitroso compounds could influence the induction of hepatocarcinogenesis [Cancer Res., 52 (15), 1992, pp 4139–4143]. Moreover, it has also been reported that L-NAME ($N^G$-nitro-L-arginine methyl ester), another nitric oxide synthase inhibitor, inhibits the formation of prostaglandin E2 (PGE2) being induced by HIV coating glycoprotein (gp) 120, and that NO contributes to the involvement of neural cells in HIV-related cerebral disorders [Biochem. Biophys. Res. Commun., 203 (1), 1994, pp 87–92].

However, all these reports are concerned with physiological implications of •NO on neural cell damages or hepatocarcinogenesis, being induced by viral infection, but as to the direct action of •NO on virus per se, there has been reported antiviral activity of •NO dependent inhibition of virus replication, as mentioned below. That is, it has been reported in Science, 261 (5127), 1993, pp 1445–1448 that it is very important to induce NO synthase in order to demonstrate inhibitory effects on replication of ectromelia virus, vaccinia virus, herpes simplex virus, by activation of γ-interferon. Besides, it has been also reported in J. Clin. Invest., 91 (6), 1993, pp 2446–2452 that •NO has inhibitory effects on protein and DNA synthesis of herpes simplex virus, i.e. •NO has an antiviral effect.

Until now, various inhibitors of •NO synthase (hereinafter, occasionally abbreviated as NOS) have been used in order to investigate the pathophysiological mechanism of •NO in the living body. Such NOS inhibitors include, for example, such substances inhibiting the induction or activation of NOS, substances inhibiting cofactors of NOS, and L-arginine analogues being competitive inhibitor for substrate of NOS. It is considered that these NOS inhibitors are useful not only for the analysis of the pathophysiological mechanism of •NO in the living body, but also can be possibly used in the treatment of cell and tissue damages, shock, ischemic diseases, etc.

Recently, the present inventors have found organic compounds rapidly reacting with •NO and strongly inhibiting physiological activities of •NO, i.e. imidazolinoxyl N-oxide derivatives (hereinafter, occasionally abbreviated as PTIO derivatives) as an •NO scavenger (Biochemistry, 32, 827–832, 1993). The PTIO derivatives are a stable organic radical species, and directly react with •NO, by which strongly inhibits the physiological activities of •NO.

There have been done various pharmacological tests on these effects of PTIO derivatives. For example, it has been reported that PTIO derivatives suppress vascular permeability caused by NO in a Sarcoma-180 solid cancer transplanted mouse (Jpn. J. Cancer Res. 85, 331–334, 1994); PTIO derivatives enhance an antibacterial activity of NO against *Cryptococcus neoformans* (Infect. Immun. 61, 3552–3555, 1993); PTIO derivatives show potent activities of maintaining blood pressure and of improving renal functions in a rat endotoxin shock model (Biochem. Biophys. Res. Commun., 202 (2), 1994, pp 923–930), etc. These reports all suggest the applicability of PTIO derivatives as an anticancer agent, an antibacterial agent, or an agent for treatment of shock, but there have never been reported as to effects of PTIO derivatives on viral infections.

Recently, it has been known in various viral infections that host immune response induced by viral infection disadvantageously affects the living body, and destroys host cells by immunological pathway, which is considered to be a diverse array of the pathogenesis mechanism. For example, in the pathogenesis in various inflammatory diseases, much attention has been focused on a role of an active oxygen, and it is reported that the level of oxygen radical ($O_2$•–) is increased greatly in the lung of mouse infected with influenza virus, and the increase thereof completely correlates with the development of severity of clinical signs. Moreover, $O_2$•– in the living body is eliminated by administering allopurinol, which is an inhibitor of xanthin oxidase (XOD) or polymer conjugated superoxide dismutase (SOD) with prolonged plasma half-life, into a virus infected mouse and as a result significant therapeutic effects are achieved. Based on these facts, it is indicated that some biofactors derived from the host such as oxygen radical may participate in the pathogenesis of viral infections.

However, there have been still many unclarified aspects of the role of biofactors in the pathogenesis during viral infections, and it has not been developed as an agent for treatment of viral infections which is highly useful in the view point of biofactors. Thus, an object of the present invention is to discover an agent for the treatment of viral infections by inhibiting viral pathogenesis.

BRIEF DESCRIPTION OF INVENTION

The present inventors have found that NOS is induced according to the development of pathological lesions (pulmonary consolidations associated with cell infiltration, hemorrhagic spot, etc.) in influenza viral pneumonia. •NO is produced by NOS, but it is indicated that overproduced •NO damages various tissues based on the chemical reactivity of •NO as a radical in cases of sepsis, endotoxin shock, arthritis, etc., as explained above. Under the above circumstances, the present inventors have intensively studied and paid much attention to that overproduced •NO may be an injury factor in the indirect pulmonary tissue injury mechanism induced by host immune response in the viral infection lesions. As a result, the present inventors have found that PTIO derivatives, •NO scavengers, can significantly ameliorate the pathogenic states of viral infection in mouse influenza virus pneumonia model, and that various •NO scavengers and NOS inhibitors are useful in the treatment of various viral infections, and have finally accomplished the present invention.

That is, an object of the present invention is to provide a method for treatment of viral infections induced by influenza virus, herpes virus, hepatitis virus, cytomegalovirus, human immunodeficiency virus, etc., which comprises administering to the patients being suffering from said viral infections an effective amount of one or more substances selected from the group consisting of •NO scavengers such as PTIO derivatives and various NOS inhibitors.

Besides, as explained above, it has been reported that •NO shows virus replication inhibitory activity, but it has not been observed that virus replicates more by the administration of the agent of the present invention as is shown in Experiment 6 hereinafter.

DETAILED DESCRIPTION OF INVENTION

Figure 1:
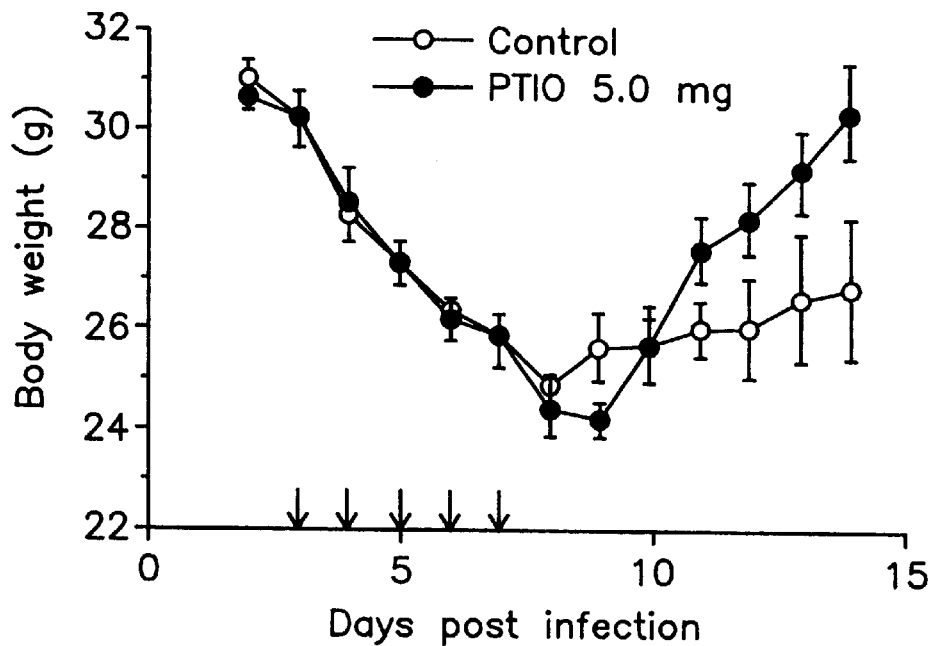
FIG. 1 illustrates the body weight recovery effect in mouse in Experiment 1, and PTIO was intraperitoneally administered once a day at the arrow point.

The present invention is illustrated hereinafter in more detail.

The compound used in the method for treatment of viral infections of the present invention includes the following •NO scavengers and NOS inhibitors.

(1) Nitric oxide radical (NO) scavengers (i) PTIO derivatives of the following formula (I), which are stable organic radical species.

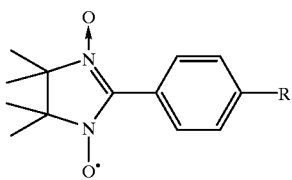

wherein R is preferably a hydrogen atom, a carboxyl group or a carboxymethoxy group. The PTIO derivatives may be in the form of a pharmaceutically acceptable salt thereof, for example, salts with an alkali metal (e.g. sodium, potassium. etc.); salts with an alkaline earth metal (e.g. magnesium, calcium, barium, etc.), ammonium salt; salts with tertiary amines (e.g. pyridine, triethylamine, tri-n-butylamine, etc.)

(ii) 3-(3,4-Dihydroxy-5-nitrobenzylidene)-2,4-pentanedione (general name: Nitecapone)

(iii) N-Methyl-D-glucamine dithiocarbamate (MGD)

(2) Nitric oxide radical synthase (NOS) inhibitors (i) Competitive inhibitor for NOS substrate L-arginine analogues such as $N^G$-nitro-L-arginine (L-NNA), $N^G$-amino-L-arginine, $N^G$-monomethyl-L-arginine (L-NMMA), $N^G,N^G$-dimethyl-L-arginine, $N^G$-nitro-L-arginine methyl ester (L-NAME), etc., or a pharmaceutically acceptable acid addition salt thereof (hydrochloride, acetate, etc.);

aminoguanidine;
7-nitroindazole;
S-ethylisothiourea;
S-methylisothiourea;
S-methylthiocitrulline;
S-ethylthiocitrulline;
N-ethylimino-L-ornithine (ii) Flavoprotein binding inhibitors diphenyleneiodonium (iii) Tetrahydrobiopterin biosynthesis inhibitors 2,4-diamino-6-hydroxypyrimidine (iv) Inhibitors of NOS induction/generation corticosteroids such as dexamethasone;
transforming growth factor(TGF)-β-1, 2 or 3;
interleukin-4;
interleukin-10;
aqueous extract of scutellaria root (v) Anti-NOS monoclonal antibodies
anti-eNOS (endothelial NOS) antibody;
anti-iNOS (inducible NOS) antibody;
anti macNOS (macrophage NOS) antibody The above active ingredients are all known compounds, and are commercially available or can be easily prepared by a conventional method. Among PTIO derivatives (I), the compound of the formula (I) wherein R is a hydrogen atom, i.e. 2-phenyl-4,4,5,5-tetramethylimidazolin-1-oxy 3-oxide (hereinafter, occasionally abbreviated as PTIO) can be prepared by the method disclosed in J. Am. Chem. Soc. 90, 1078, 1968. The compound of the formula (I) wherein R is a carboxyl group, i.e. 2-(4-carboxyphenyl)4,4,5,5-tetramethyl-imidazolin-1-oxy 3-oxide (hereinafter, occasionally abbreviated as carboxy-PTIO) can be prepared by neutralizing an aqueous 2,3-bis(hydroxyamino)-2,3-dimethylbutyl sulfuric acid ester solution with an aqueous potassium hydrogen carbonate solution, adding thereto 4-formylbenzoic acid, stirring the resulting 1,3-dihydroxy-4,4,5,5-tetramethyl-2-(4-carboxyphenyl) tetrahydroimidazole in N,N-dimethylformamide in the presence of lead dioxide, filtering the solution, concentrating the aqueous layer of the filtrate, adjusting the pH value thereof to pH 8.0, and followed by lyophilizing the product to give carboxy-PTIO potassium salt (Biochemistry, 32, 827–832, 1993). Moreover, the compound of the formula (I) wherein R is a carboxymethoxy group, i.e. 2-[4-(carboxy-methoxy) phenyl]-4,4,5,5-tetramethylimidazolin-1-oxy 3-oxide (hereinafter, occasionally abbreviated as carboxymethoxy-PTIO) can be obtained in the form of carboxymethoxy-PTIO potassium salt in the same manner as in the preparation of carboxyl-PTIO mentioned above, except that 4-formylphenoxy-acetic acid is used instead of 4-formylbenzoic acid (Biochemistry, 32, 827–832, 1993).

These PTIO derivatives can directly react with •NO in the living body as described in the following scheme, and convert •NO into •NO$_2$, by which overproduced •NO can be reduced. Besides, •NO$_2$ per se thus produced is considered to have an antiviral effect without physiological effect of NO, and •NO$_2$ is converted into non-toxic HNO$_2$ or HNO$_3$ by a normal metabolism pathway.

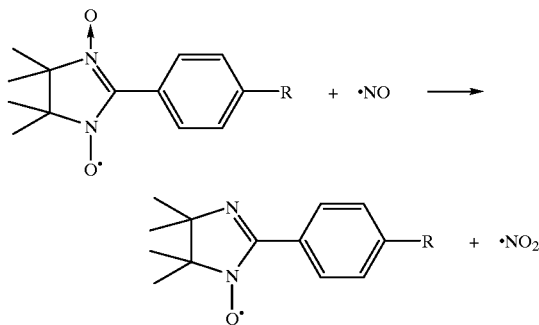

The above three kinds of PTIO derivatives are different each other in solubility in water, but the reactivity to •NO of each PTIO derivative is the same, and hence, any one of these can be used in the present invention. Besides, these derivatives may be used alone, or in mixture of two or more in the present invention.

Further, Nitecapone, another •NO scavenger, can be commercially available from Orion-Farmos Pharmaceuticals (Espoo, Finland). L-Arginine analogues being NOS inhibitors, for example, L-NMMA can be prepared by the method disclosed in Acta. Biochim. Biophys., Acad. Sci. Hung., 12, 191–196 (1977). N-Ethylimino-L-ornithine can be prepared by the method disclosed in Journal of Antibiotics, 25 179–184 (1972). Diphenyleneiodonium can be prepared by the method disclosed in J. Am. Chem. Soc. 78, pp 3819–3820.

When administering the above mentioned compound which is an active ingredient of the present invention to a virus infected mouse, a significant body weight recovery and a high survival rate are obtained, and it means that the above-mentioned active ingredient can effectively treat pathogenic states induced by viral infection. The pharmacological activities of the active ingredient of the present invention mentioned above will be based on the elimination activity of •NO and hence •NO derived derivatives, or the inhibitory activity of excessive production of •NO, which is induced by host response to viral infection and is considered to be an endogenous injury factor during infection. The overproduction of •NO is induced in the host upon microbial (viral) infection due to the induction of NOS by the infection to the excessive extent.

The pharmacological effects of the active ingredients of the present invention can be effective in any viral infections which would induce the overproduction of •NO; for example, it is particularly effective in infections by influenza virus, herpes virus, hepatitis virus, cytomegalovirus, human immunodeficiency virus (HIV), etc.

The method for treatment of viral infections of the present invention shows the desired therapeutic effects thereof by eliminating and treating the pathogenesis induced by viral infection with removing the biofactors for injury which may be induced by viral infection.

The active ingredient used in the method for treatment of viral infections of the present invention may be used in the form of a pharmaceutical preparation being suitable for oral or parenteral administration. When administered orally, the active ingredient of the present agents is used in the form of a pharmaceutical preparation such as powders, granules, tablets, capsules, troches, liquids, syrups, medicinal oils, liposome, emulsion, etc., which are prepared by mixing an active ingredient with a pharmaceutically acceptable additive (e.g. carrier, vehicle, diluent, etc.). When administered parenterally, the active ingredient of the present agent is used in the form of injection preparation such as solution or suspension for intravenous drip infusion, intravenous injection, intramuscular injection, subcutaneous injection, etc., or in the form of suppositories. The amount of the active ingredient to be contained in the pharmacological preparation may be selected properly and may not be necessarily specified.

For example, a medicinal oil preparation of a PTIO derivative can be prepared by dispersing uniformly an active ingredient in a medium or higher fatty acid glyceride. The medium or higher fatty acid glyceride used therein is a mono-, di- or triglyceride of a saturated fatty acid having 6 to 20 carbon atoms. Representative ones of the above fatty acid glyceride are a mono-, di- or triglyceride of caprylic acid, capric acid, lauric acid, myristic acid, palmitic acid, oleic acid, etc. These fatty acid glycerides may be used alone or in the form of a mixture thereof.

The fatty acid glycerides include either natural, synthetic or semi-synthetic ones, but it is usually convenient to use a natural vegetable oil. The vegetable oil which can be used in the present invention may preferably be olive oil (oleic acid; 70–85%, linoleic acid; 4–12%, palmitic acid; 7–15%), corn oil (linoleic acid; 40–60%, palmitic acid; 25–45%), sesame oil (oleic acid; 35–46%, linoleic acid; 35–48%), camellia oil, coconut oil (lauric acid; 45–52%, capric acid; 4–12%, caprylic acid; 6–10%), palm oil, etc. The commercially available vegetable oils can be used in the present invention as they are. The commercially available medium fatty acid triglyceride is, for example, Panaceto 875™, ibid. 810, ibid. 800 (the content of caprylic acid; 10–100%) manufactured by NOF Corporation., ODO™ (the content of caprylic acid; 67%) manufactured by Nisshin Oil Co. Ltd. The commercially available medium fatty acid monoglyceride is, for example, Homoteques PT™ (the content of caprylic acid; about 60%) manufactured by Kao Corp., and the commercially available mixture of a medium fatty acid monoglyceride and a medium fatty acid diglyceride is, for example, Witafrol™ manufactured by Dynamite Nobel Co., Ltd. The commercially available higher fatty acid triglyceride is, for example, olive oil marketed by Wako Pure Chemical Industries Ltd., linoleic acid manufactured by NOF Corporation, or other cooking oils on the market.

The pharmaceutical preparation used in the present method for treatment of viral infections can be formulated by a conventional method which should be selected according to the respective formulation. For example, in order to prepare the above-mentioned medicinal oil preparation of a PTIO derivative, a lyophilized powder of an aqueous solution of an active ingredient, the pH value of which is previously adjusted to a desired value (pH 6.8–7.5), is added to a fatty acid glyceride being previously supplemented with or without an amphiphilic detergent and/or a lower alkanol, and the mixture is dispersed uniformly to give a uniform dispersion. Alternatively, a mixture of a solution of an active ingredient in an aqueous ammonium carbonate solution and an aqueous amphiphilic detergent solution and/or a lower alkanol is lyophilized, and to the resulting lyophilized powder is added a medium or higher fatty acid glyceride solution, and then the mixture is dispersed uniformly to give a uniform dispersion under sonifier if necessary. The resulting dispersion thus obtained is further treated in a conventional manner which is selected according to the desired type of preparation to give the agent for treatment of viral infections of the present invention.

The amphiphilic detergent used therein is a non-toxic substance being both hydrophilic and lipophilic. Representative ones of the amphiphilic detergents are, for example, natural amphoteric surfactants, polyglycerine fatty acid esters, polyoxyethylene sorbitan fatty acid esters (Tween), sorbitan fatty acid esters (Span), polyethylene glycol, etc. The natural amphoteric surfactants are preferably soy bean phospholipid, yolk lecithin, and analogues thereof, for example, Phosphatidyl choline, Yolk lecithin, Soy bean lecithin, Phosphatidyl ethanolamine, all manufactured by NOF Corporation, and the like. The polyglycerine fatty acid ester is, for example, Unigly (manufactured by NOF Corporation). The polyoxyethylene sorbitan fatty acid ester is, for example, Tween 20™ manufactured by Wako Pure Chemical Industries, Ltd. The sorbitan fatty acid ester is, for example, Span 20™ manufactured by Wako Pure Chemical Industries, Ltd. The polyethylene glycol is, for example, PEG 6000. In addition, the anion surfactant is, for example, sodium laurylsulfate, and the cation surfactant is, for example, benzalkonium chloride, benzethonium chloride, Eizon™ manufactured by Nelson Res. & Dev. The lower alkanol is, for example, ethanol, propanol, isopropanol, butanol, etc. The amino acid or a derivative thereof (i.e. fatty acid ester of 5-oxo-2-pyrrolidine carboxylic acid) may also be used.

The fatty acid glyceride is used in an amount of 0.1 to 100 ml, preferably in an amount of 0.5–5 ml, to 1 mg of the active ingredient. The amphiphilic detergent and the lower alkanol may not be always necessarily added, but when they are added, the wetting effect against oil is exhibited, and the dispersion-solubility is enhanced to give a stable pharmaceutical preparation, as well as the absorption promoting effect is also exhibited. The amount of an amphiphilic detergent varies according to the kinds thereof. For example, a liquid detergent is usually used in an amount of 0.01–0.1 ml, and a solid detergent is usually used in an amount of 0.05–5 mg, to 1 mg of the active ingredient. The amount of the lower alkanol is in the range of 1–15% by weight to the whole weight of the preparation. By the addition of a lower alkanol, there is obtained a more uniform dispersion of an active ingredient.

The dose of the pharmaceutical preparation used in the present method for treatment of viral infections for human varies according to ages, weights and conditions of the patients, and the administration routes to be employed. When administered by intravascular drip infusion, the dose of the present pharmaceutical preparation is usually in the range of 100 mg–5 g of the active ingredient per day, preferably in the range of 200 mg to 2 g of the active ingredient per day for an adult.

The present invention is illustrated in more detail by the following Experiments and Examples, but should not be construed to be limited thereto.

Experiment 1 ddY Mice (5–6 weeks old, weight; about 30 g) were infected with influenza virus [$A_2$/Kumamoto ($H_2N_2$)] by intranasal spray of $LD_{50}$ units of the virus. For five days from day 3 post-infection, PTIO was intraperitoneally administered to the mice at a dose of 5 mg per mouse once a day. PTIO was used in the form of a medicinal oil preparation which was prepared by dissolving PTIO (10 mg) in oil base (1 ml, Panaceto 875™ (manufactured by NOF Corporation). In the control group, a medicinal oil preparation containing no PTIO (0.5 ml per mouse) was intraperitoneally administered to the mice once a day. Each group contains 10 mice, and the effects of PTIO on the body weight recovery and the survival rate of mice are shown in FIG. 1 and FIG. 2, respectively.

Figure 2:
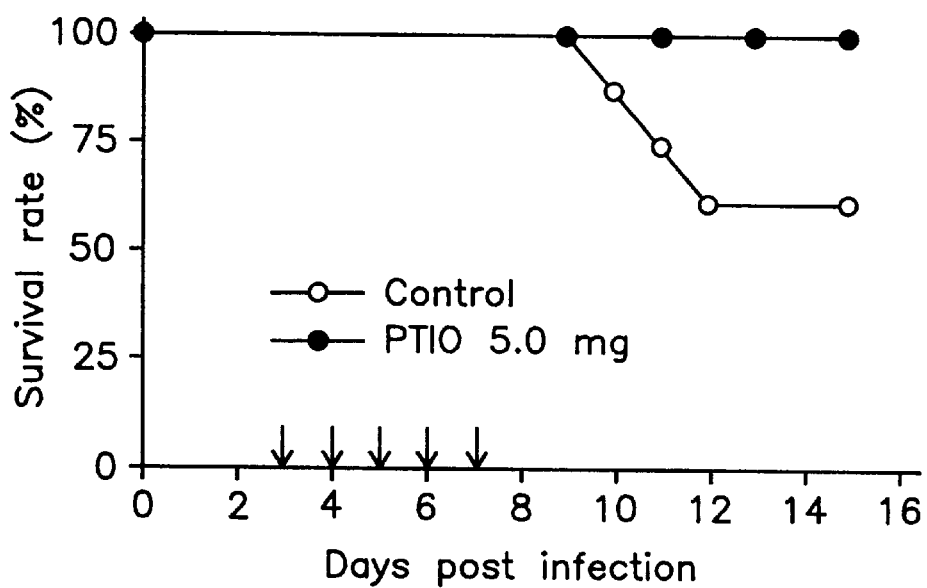
FIG. 2 illustrates the survival rate of mouse in Experiment 1, and PTIO was intraperitoneally administered once a day at the arrow point.

As is apparent from FIG. 1 and FIG. 2, the mice in the PTIO-treated group showed the rapid recovery of body weight, as compared with the mice in the control group. The survival rate of the mice in the PTIO-treated group was 100% while that of the mice in the control group was 60%. From these results, the PTIO medicinal oil preparation of the present invention was proved to have a therapeutic effect in influenza virus infected mice.

Experiment 2

The same procedures as those in Experiment 1 were performed except that carboxyl-PTIO or carboxymethoxy-PTIO was used instead of PTIO. The similar results to those of Experiment 1 were obtained.

Experiment 3

Figure 3:
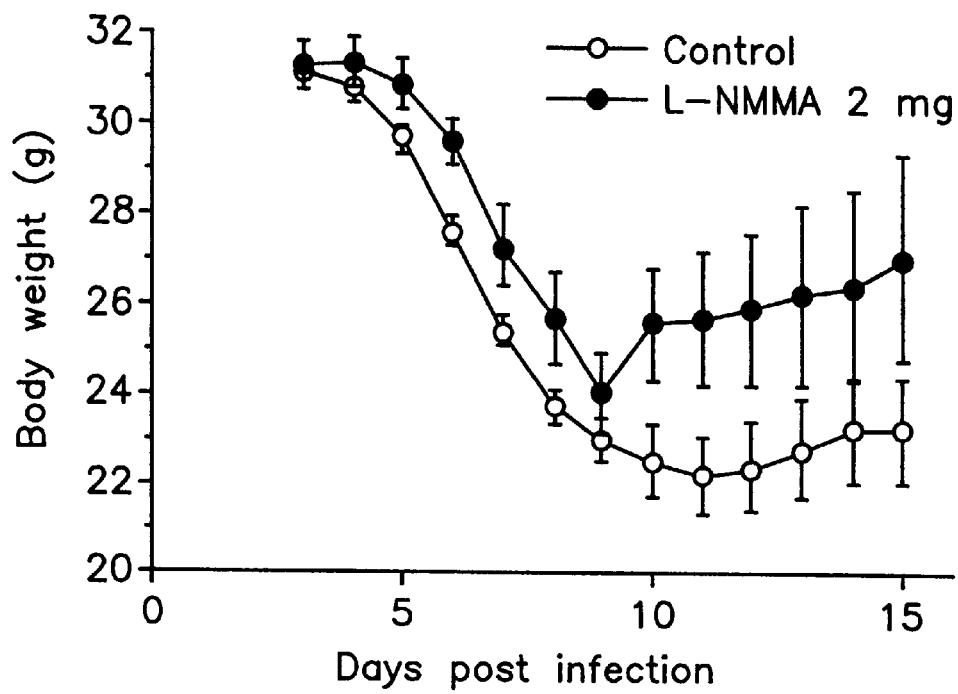
FIG. 3 illustrates the inhibitory effect of L-NMMA acetate on body weight loss of mouse in Experiment 3.
Figure 4:
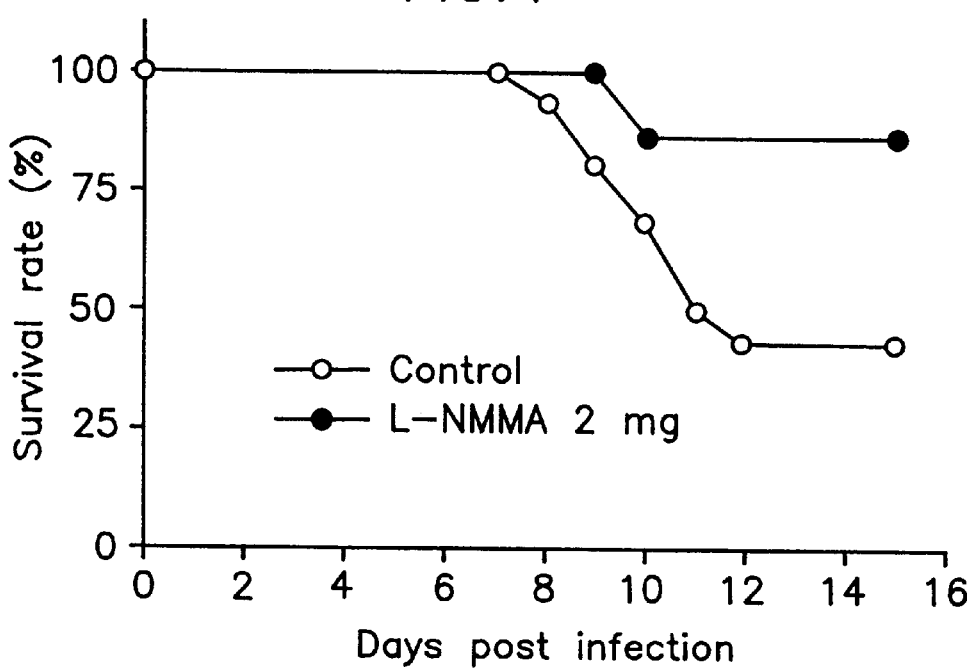
FIG. 4 illustrates the survival rate of mouse by L-NMMA acetate in Experiment 3.

The same procedures as those in Experiment 1 were performed except that a physiological saline solution containing L-NMMA acetate (dose; 2 mg of L-NMMA acetate/day/mouse) was used instead of PTIO. The effects of L-NMMA acetate on the body weight recovery and the survival rate of mice are shown in FIG. 3 and FIG. 4, respectively. As is shown in the results, the body weight loss was suppressed, and the higher survival rate was apparently achieved in the L-NMMA acetate-treated group, as compared with those of the control group.

Experiment 4

Figure 5:
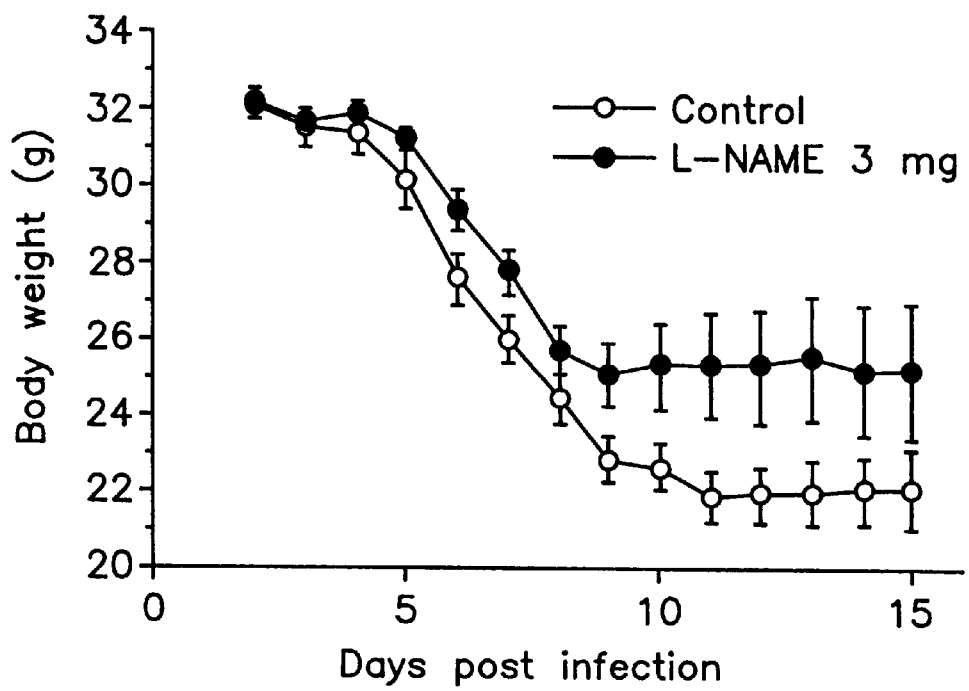
FIG. 5 illustrates the inhibitory effect of L-NAME on body weight loss of mouse in Experiment 4.
Figure 6:
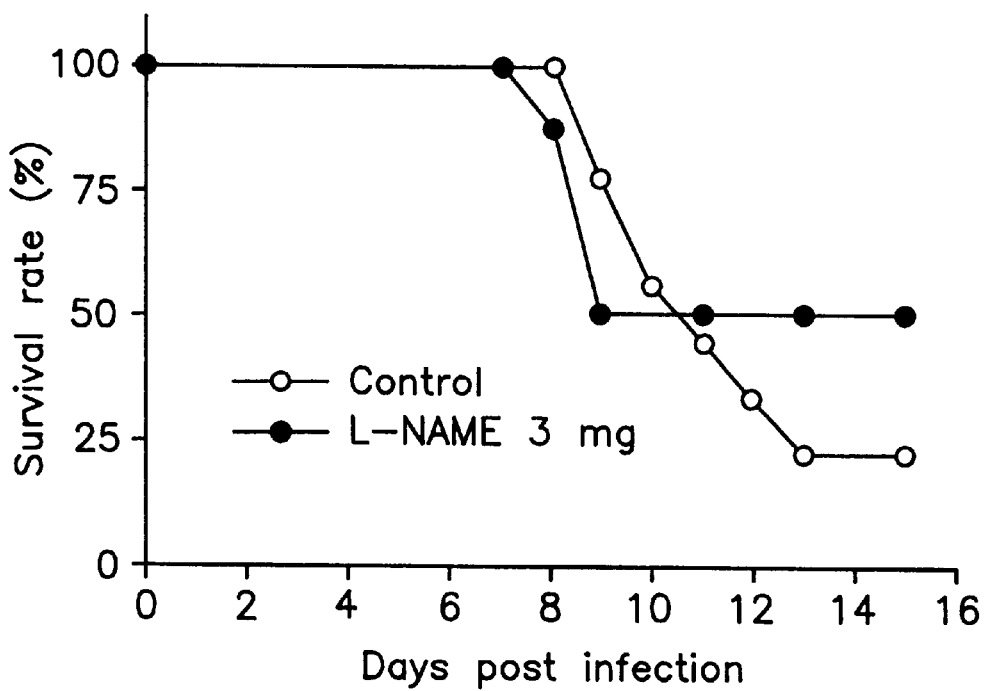
FIG. 6 illustrates the survival rate of mouse by L-NAME in Experiment 4.

The same procedures as those in Experiment 1 were performed except that a physiological saline solution containing L-NAME (dose; 3 mg of L-NAME/day/mouse) was used instead of PTIO. The body weight recovery and the survival rate of mice were studied, and the results thereof are shown in FIG. 5 and FIG. 6, respectively. As is shown in the results, the body weight loss was suppressed, and the higher survival rate was apparently achieved in the L-NAME-treated group, as compared with those of the control group.

Experiment 5

Figure 7:
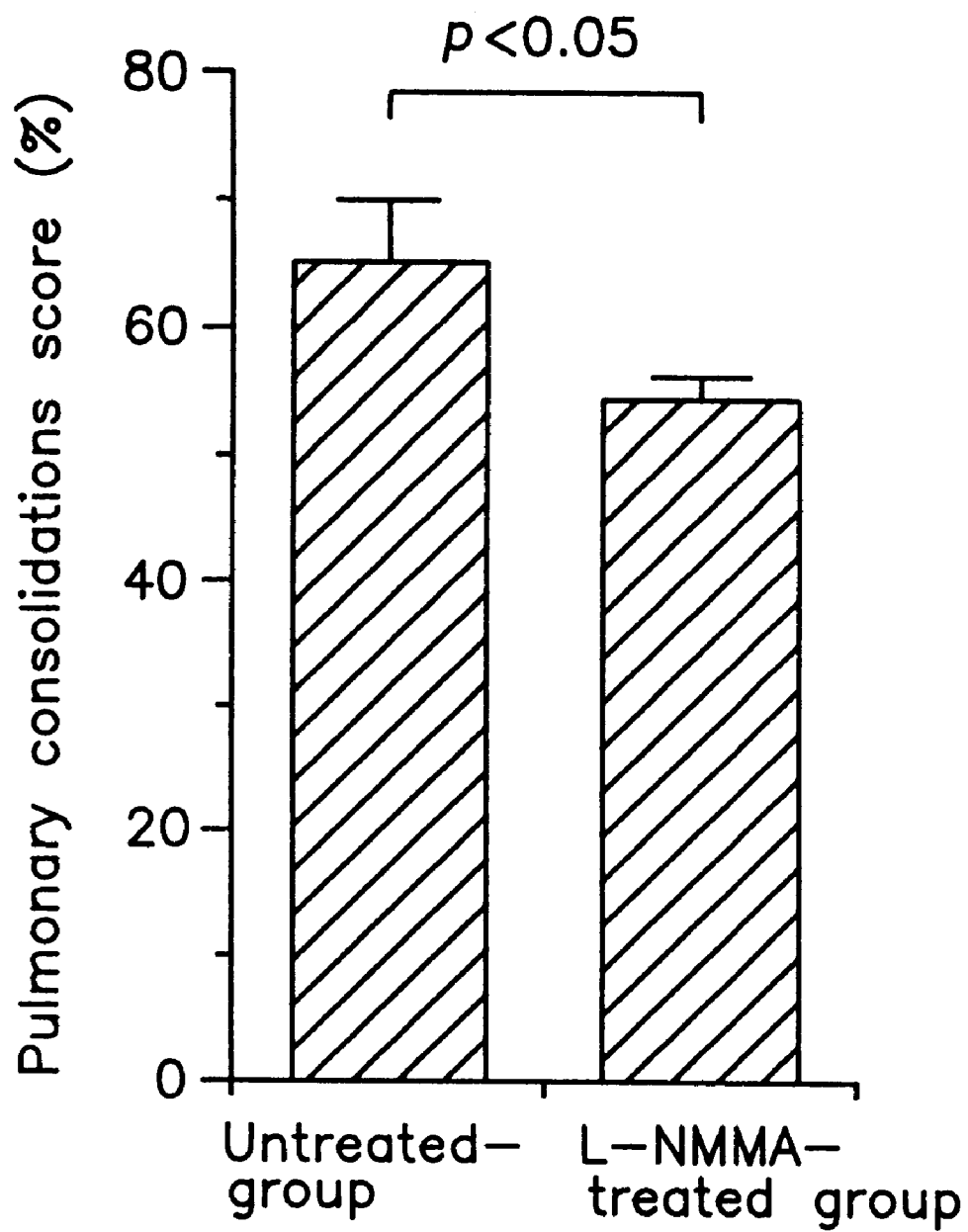
FIG. 7 illustrates the evaluation results of pulmonary consolidations of mouse in Experiment 5.

To ddY mice (5–6 weeks old, weight; about 30 g, 5 mice) being infected with influenza virus in the same manner as in Experiment 1 were intraperitoneally administered a physiological saline solution containing L-NMMA acetate (dose; 2 mg of L-NMMA acetate/day/mouse) for four days from day 3 post-infection. On day 6 post-infection, the mice were sacrificed to examine the pulmonary consolidations thereof according to the method disclosed in Journal of Experimental Medicine, 70, 209 (1939). As a control, the lung of the mice which were not treated with a NOS inhibitor was also examined. The results are shown in FIG. 7. As is clear from FIG. 7, fewer pulmonary consolidations were observed in the mice of the L-NMMA acetate-treated group than in the control mice.

Further, since it has been reported that •NO shows an antiviral activity, the following experiment was done in order to prove that the elimination of •NO and the inhibition of •NO production would not accelerate virus replication.

Experiment 6

Figure 8:
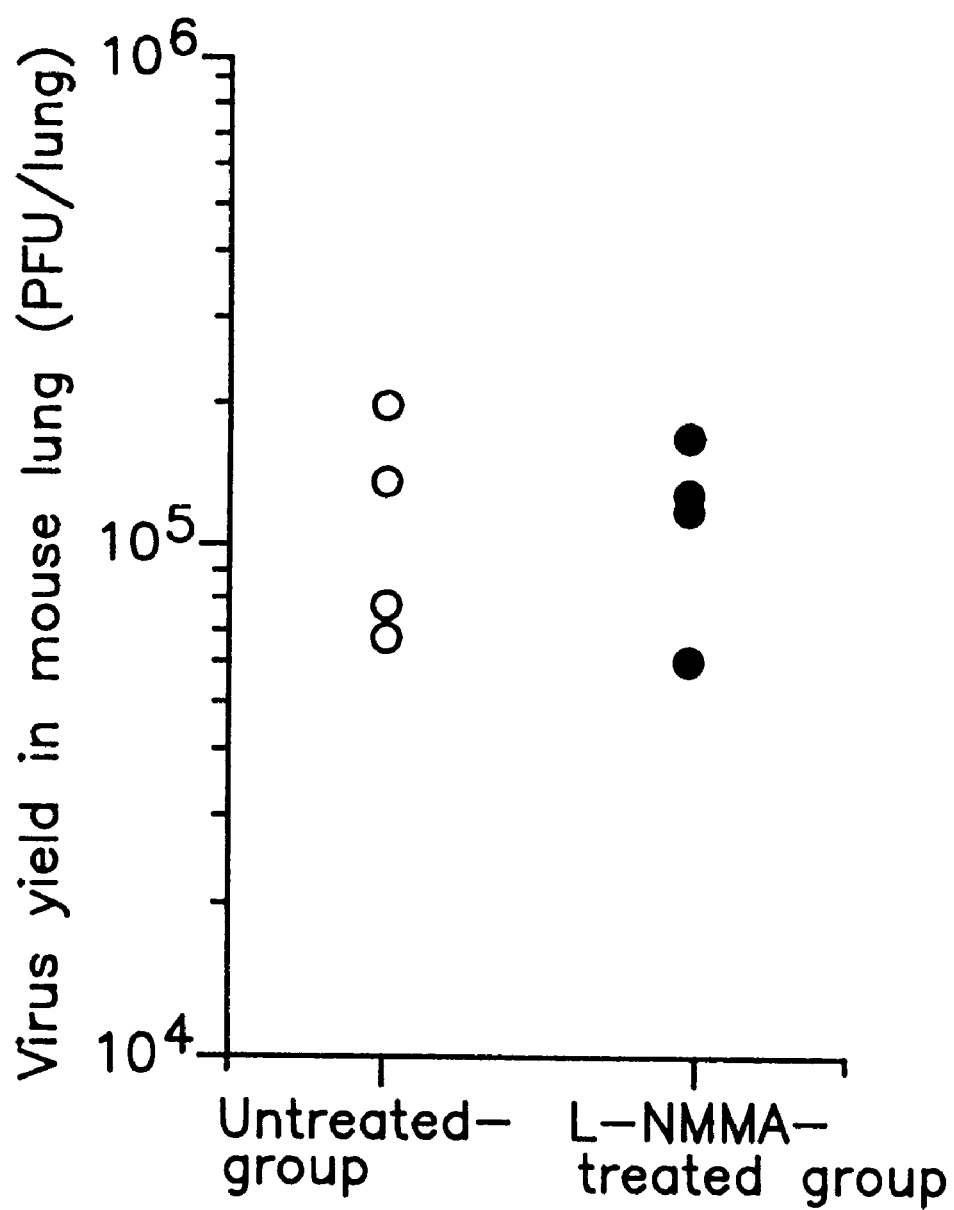
FIG. 8 illustrates the virus yield in mouse lung in Experiment 6.

Four mice were infected with influenza virus, and then were administered with a physiological saline solution containing L-NMMA acetate in the same manner as in Experiment 5. On day 6 post-infection, the virus yield in the mouse lung was determined by plaque-forming assay. As a control, the virus yield in the mouse lung which was not treated with an NOS inhibitor was also determined likewise. The results are shown in FIG. 8. The virus yield in the mouse lung of the L-NMMA acetate-treated group was almost the same as that of the control group, by which it was proved that the elimination of •NO and the inhibition of the production thereof do not accelerate virus replication.

Experiment 7

Rats were infected with herpes simplex virus type I, HSV-1 by intranasal spray of 10-fold units of $LD_{50}$ units of the virus to give a rat encephalitis model. For five days from day 3 post-infection, L-NMMA acetate was intraperitoneally administered to the rats at a dose of 100 mg/kg once a day. In the control group, a physiological saline solution was administered to rats instead of L-NMMA acetate likewise.

Figure 9:
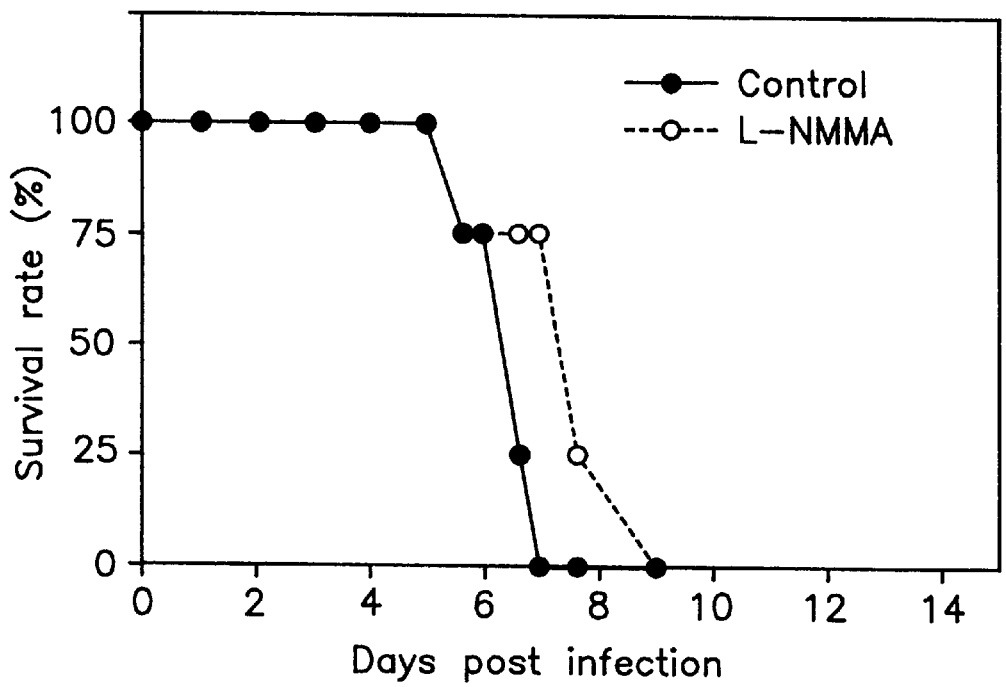
FIG. 9 illustrates the survival rate of mouse by L-NMMA acetate in Experiment 7.

The survival rate of rats post infection is shown in FIG. 9.

As is apparent from FIG. 9, the apothanasia effect of about one day was observed in the rats treated with L-NMMA acetate.

Experiment 8

Rats were infected with HSV-1 at 1.3-fold units of $LD_{50}$ units thereof in the same manner as in Experiment 7, and L-NMMA acetate was administered to the rats in the same manner as in Experiment 7. In the control group, a physiological saline solution was administered to rats instead of L-NMMA acetate likewise.

Figure 10:
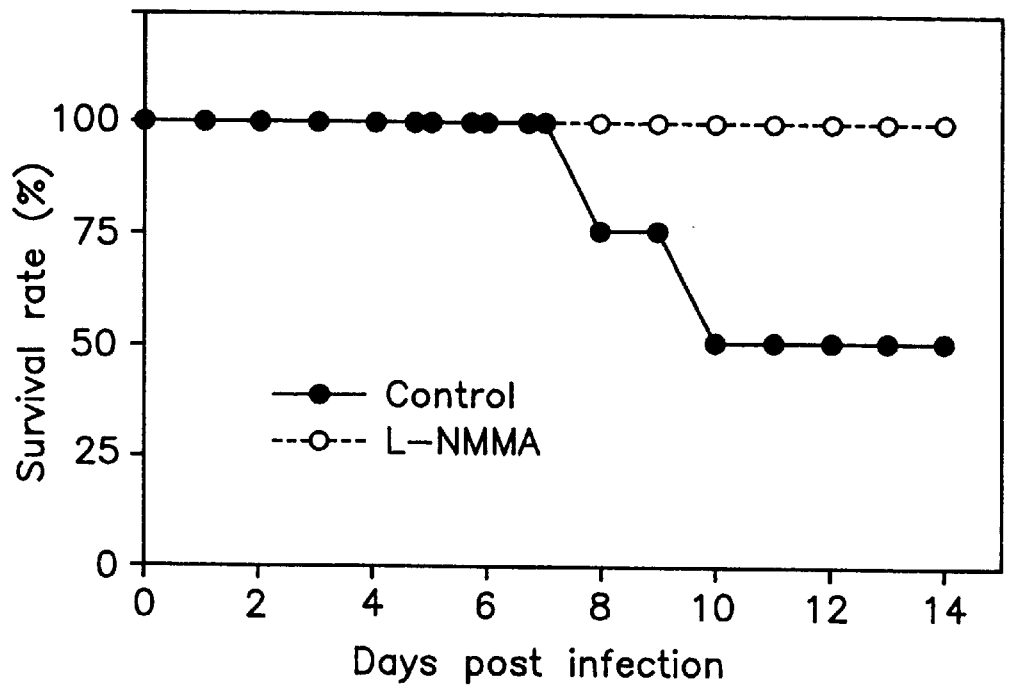
FIG. 10 illustrates the survival rate of mouse by L-NMMA acetate in Experiment 8.

The survival rate of rats post infection is shown in FIG. 10.

As is apparent from FIG. 10, the lethal rate was reduced in the rats treated with L-NMMA acetate.

By Experiments 7 and 8, it was confirmed that the present invention shows a therapeutic effect in a rat encephalitis model infected with herpes simplex virus type I.

EXAMPLE 1

PTIO (1.0 g) is suspended and dissolved by sonication in Panaceto 875™ (manufactured by NOF Corporation) with shaking so as to be solubilized to give a medicinal oil preparation of PTIO.

EXAMPLE 2

Phosphatidyl chlorine (50 mg) is added to a distilled water (1 ml), and the mixture is treated with ultrasonic so as to be solubilized. The solution thus obtained and a solution of carboxy-PTIO powder in 0.02% aqueous ammonium carbonate solution under ice-chilled (50 mg/ml) were mixed in equal volume, and the mixture is stirred and lyophilized. To the lyophilized powder (100 mg) is added Panaceto 875™ (30 ml), and the mixture is treated under ultrasonic in an ice-water bath for 30 seconds to give a liquid preparation of carboxy-PTIO.

EXAMPLE 3

Carboxy-PTIO (100 mg) is dissolved in 5.0% sodium hydrogen carbonate solution (20 ml) to give a water-soluble injection preparation. Carboxymethoxy-PTIO can also be treated likewise to give a water-soluble injection preparation thereof.

INDUSTRIAL APPLICABILITY OF THE INVENTION

The method for treatment of viral infections of the present invention comprises administering to the patients being suffering from said viral infections a substance which can effectively eliminate •NO or inhibit •NO production, which is excessively produced by host response to infection when infected with virus, and the present method is useful in the treatment of pathogenic states induced by infection with virus such as influenza virus, herpes virus, hepatitis virus, cytomegalovirus, human immunodeficiency virus, etc. Therefore, the method of the present invention can be employed to the prophylaxis or treatment of these viral infections.

What is claimed is:

1. A method for treatment of a viral infection which comprises:

administering to a patient suffering from said viral infection an effective amount of one or more substance selected from the group consisting of a nitric oxide scavenger and a nitric oxide synthase inhibitor, wherein the nitric oxide scavenger and the nitric oxide synthase inhibitor are selected from the group consisting of the following compounds:

imidazolinoxyl N-oxide derivatives of the formula (I):

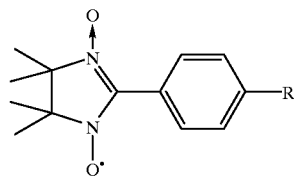

(I)

wherein R is a hydrogen atom, a carboxyl group, a carboxymethoxy group, or a pharmaceutically acceptable salt thereof, 3-(3,4-dihydroxy-5-nitrobenzylidene)-2,4-pentadione, N-methyl-D-glucamine dithiocarbamate, L-arginine analogues selected from $N^G$-nitro-L-arginine, $N^G$-amino-L-arginine, $N^G$-monomethyl-L-arginine, $N^G$, $N^G$-dimethyl-L-arginine, $N^G$-nitro-L-arginine methyl ester, or a pharmaceutically acceptable acid addition salt thereof, aminoguanidine, 7-nitroindazole, S-ethylisothiourea, S-methylisothiourea, S-methylthiocitrulline, S-ethylthiocitrulline, N-ethylimino-L-ornithine, diphenyleneiodonium, 2,4-diamino-6-hydroxypyrimidine, TGFβ-1,2 or 3, interleukin-4, interleukin-10, and anti-NOS monoclonal antibodies.

2. The method of treatment of a viral infection according to claim 1, which comprises administering to a patient suffering from said viral infection an effective amount of the imidazolinoxy N-oxide derivative of the formula (I).

3. The method for treatment of a viral infection according to any one of claims 1, 2, which is for treatment of an infection induced by influenza virus, herpes virus, hepatitis virus or cytomegalovirus.

4. The method for treatment of a viral infection according to any one of claims 1, 2, which is for treatment of an infection induced by influenza virus.

5. The method for treatment of a viral infection according to any one of claims 1, 2, which is for treatment of an infection induced by herpes simplex virus I.

6. The method for treatment of a viral infection according to claim 1, which comprises administering to a patient suffering from an infection induced by influenza virus an effective amount of the imidazolinoxy N-oxide derivative of the formula (I) or a pharmaceutically acceptable salt thereof, or the L-arginine analogue or a pharmaceutically acceptable acid addition salt thereof.

7. The method for treatment of a viral infection according to claim 1, which comprises administering to a patient suffering from an infection induced by herpes simplex virus I an effective amount of the L-arginine analogue or a pharmaceutically acceptable acid addition salt thereof.

8. The method of treatment of a viral infection according to claim 2, wherein R of the imidozolinoxy N-oxide derivative of the formula (I) is a hydrogen atom.

* * * * *